United States Patent [19]

Tsushima et al.

[11] Patent Number: 4,576,933

[45] Date of Patent: Mar. 18, 1986

[54] METHOD OF USE OF 1-(ALKYL FOR ALKYLCARBANOYL)-2-CARBAMOYL-GLYCEROL DERIVATIVES

[75] Inventors: Susumu Tsushima, Suita; Kohei Nishikawa, Kyoto, both of Japan

[73] Assignee: Takeda Chemical Industries, Ltd., Osaka, Japan

[21] Appl. No.: 490,224

[22] Filed: Apr. 29, 1983

[30] Foreign Application Priority Data

May 6, 1982 [JP] Japan .................. 57-76224

[51] Int. Cl.[4] .............. A61K 31/42; A61K 31/425; A61K 31/44; A61K 31/685
[52] U.S. Cl. ........................ 514/77; 514/83; 514/85; 514/89; 514/90; 514/91; 514/92; 546/22; 544/108; 544/157; 544/159; 544/404; 548/112; 260/239 E; 558/172
[58] Field of Search ............ 546/22; 548/112; 260/945; 544/108, 157, 159, 404; 514/77, 83, 85, 89, 90, 91, 92

[56] References Cited

FOREIGN PATENT DOCUMENTS 003537 9/1981 European Pat. Off. .............. 546/22

OTHER PUBLICATIONS

Central Patents Index Basic Abstracts Journal, Section B: Farmdoc, 12005C/07 B05 Toya 22.06.78 J55002-636 (Apr. 9, 1980).
Biochemical and Biophysical Research Communications, vol. 90, pp. 1194-1200 (1979).
Hypertention, vol. 3, (Supp I), p. I-107-I-111, (1981).
Rinshokagaku (The Journal of Clinical Science), vol. 17, pp. 1462-1467 (1981).

*Primary Examiner*—Alan L. Rotman
*Attorney, Agent, or Firm*—Wegner & Bretschneider

[57] ABSTRACT

Glycerol derivatives, inclusive of salts thereof, of the formula

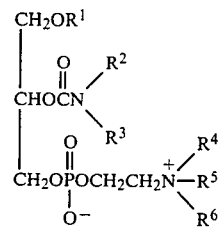

wherein $R^1$ is alkyl or alkylcarbamoyl containing 10 to 30 carbon atoms, $R^2$ and $R^3$ are independently hydrogen, $C_{1-6}$ alkyl or, taken together with the adjacent nitrogen atom, form cyclic amino, and

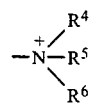

represents cyclic ammonio, and of the formula

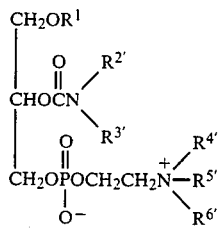

wherein $R^1$ is as defined above, $R^{2'}$ and $R^{3'}$ are $C_{1-6}$ alkyl or, taken together with the adjacent nitrogen atom, form cyclic amino and $R^{4'}$, $R^{5'}$ and $R^{6'}$ are independently hydrogen or $C_{1-6}$ alkyl, are useful as antihypertensive agents.

17 Claims, No Drawings

METHOD OF USE OF 1-(ALKYL FOR ALKYLCARBANOYL)-2-CARBAMOYLGLYCEROL DERIVATIVES

This invention relates to novel glycerol derivatives, which have hypotensive activites. More particularly, this invention relates to glycerol derivatives of the formula

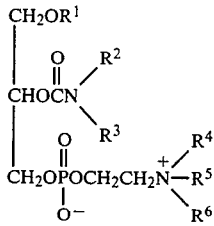
(I)

wherein $R^1$ is alkyl or alkylcarbamoyl containing 10 to 30 carbon atoms, $R^2$ and $R^3$ are independently hydrogen, lower alkyl or, taken together with the adjacent nitrogen atom, form cyclic amino, and

represents cyclic ammonio, and of the formula

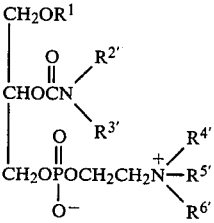
(I')

wherein $R^1$ is as defined above, $R^{2'}$ and $R^{3'}$ are lower alkyl or, taken together with the adjacent nitrogen atom, form cyclic amino, and $R^{4'}$, $R^{5'}$ and $R^{6'}$ are independently hydrogen or lower alkyl, and salts thereof, to processes for producing the compounds (I) and (I') and their use.

Referring to the above formulae (I) and (I'), the alkyl group of 10 to 30 carbon atoms represented by $R^1$ includes straight-chain and branched-chain alkyl groups such as n-dodecyl, n-tridecyl, n-tetradecyl, 3,7,11-trimethyltetradecyl, n-pentadecyl, n-heptadecyl, n-octadecyl, n-eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc. Preferred are $C_{12-20}$ alkyl groups.

The alkylcarbamoyl group of 10 to 30 carbon atoms represented by $R^1$ includes various alkylcarbamoyl groups whose alkyl moieties correspond to the above-mentioned alkyl groups.

The lower alkyl group represented by $R^2$, $R^{2'}$, $R^3$, $R^{3'}$, $R^{4'}$, $R^{5'}$ and $R^{6'}$ includes, for example, $C_{1-6}$ alkyl groups (e.g. methyl, ethyl, propyl, isopropyl, butyl, isobutyl, sec-butyl, tert-butyl, pentyl, hexyl).

The cyclic amino group which is formed by $R^2$ and $R^3$ or by $R^{2'}$ and $R^{3'}$, taken together with the adjacent nitrogen atom, includes 3- to 6-membered cyclic amino groups such as piperidino, morpholino, thiomorpholino, 1-piperazinyl, 1-pyrrolidinyl, 1-azetidinyl and 1-azilidinyl, etc.

The cyclic ammonio group represented by

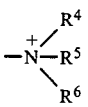

includes pyridinio, oxazolio, thiazolio, pyridazinio, quinolinio, isoquinolinio, etc., among which the 5- or 6-membered cyclic ammonio group is desirable. Any of such groups may be further substituted by $C_{1-4}$ alkyl groups (e.g. methyl, ethyl), hydroxy, hydroxyethyl, aminoethyl, amino(imino), carbamoyl, ureido, etc. The above-mentioned cyclic ammonio group includes N-methylmorpholinio, morpholinio, N-methylpiperazinio, piperazinio or the like in case that any two of $R^4$, $R^5$ and $R^6$ form a ring with the quaternary nitrogen atom with the remaining one group being hydrogen or lower alkyl. That is to say, in case that one of $R^4$, $R^5$ and $R^6$ is hydrogen (for example, $R^4$ is hydrogen), the compound (I) may be represented by the formula

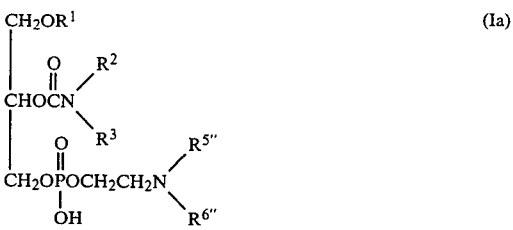
(Ia)

wherein $R^{5''}$ and $R^{6''}$, taken together with the adjacent nitrogen atom, form cyclic amino, and all the other symbols are as defined above. Similarly, when at least one or more of $R^{4'}$, $R^{5'}$ and $R^{6'}$ are hydrogen (for example, when $R^{4'}$ is hydrogen), the compound (I') may be represented by the formula

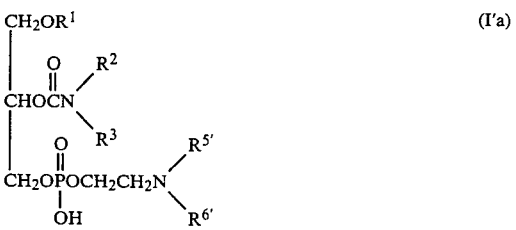
(I'a)

wherein all symbols are as defined above.

The compounds (I) and (I') may also exist in the form of salts such as salts of the formulae

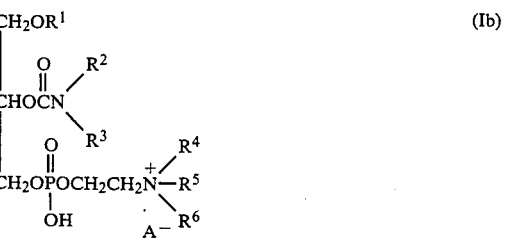
(Ib)

-continued

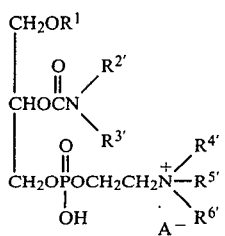 (I'b)

wherein A⁻ is an anion such as chlorine, bromine, iodine, tosyl ion, etc., and all the other symbols are as defined above, and salts of the formulae

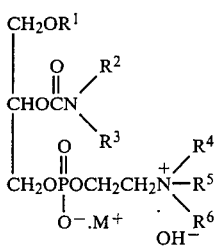 (Ic)

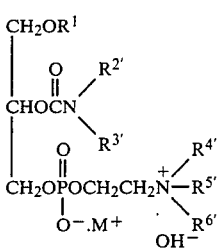 (I'c)

wherein $M^+$ is an alkali metal (e.g. sodium, potassium) ion or an alkaline earth metal (e.g. calcium, magnesium) ion, and all the other symbols are as defined above.

The above compound (I) can be produced, for example, by the following processes.

Process A

A compound of the formula

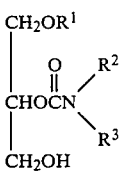 (II)

wherein all symbols are as defined above, is reacted with a compound of the formula

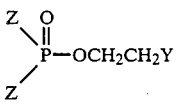 (III)

wherein Y and Z are halogen (e.g. chlorine, bromine, iodine) to give a compound of the formula

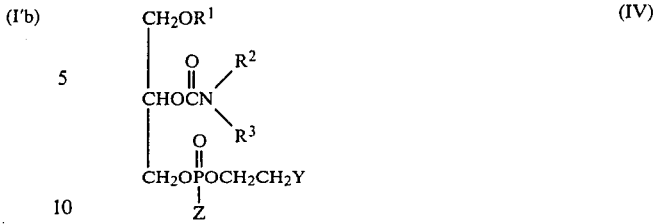 (IV)

wherein all symbols are as defined above. Then water is allowed to act on the compound (IV) to give a compound of the formula

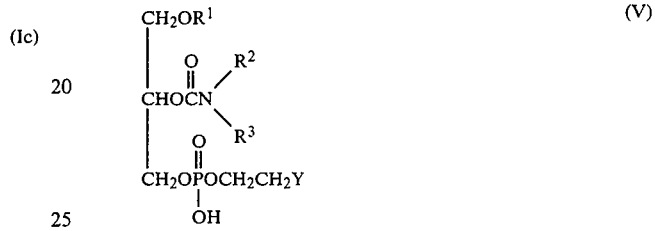 (V)

wherein all symbols are as defined above.

The compound (V) can also be produced by converting a compound of the formula

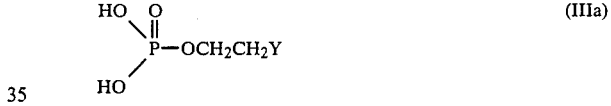 (IIIa)

wherein Y is as defined above, to an active derivative thereof and, then, reacting the latter with the compound (II).

Reaction of the compound (V) with a compound of the formula

 (VI)

wherein all symbols are as defined above, gives compound of the formula (I).

The compound (II) can be produced, for example, by the following processes.

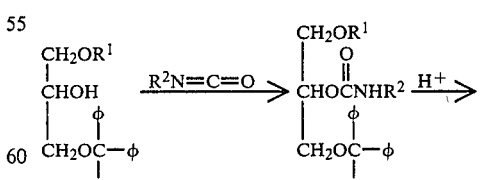

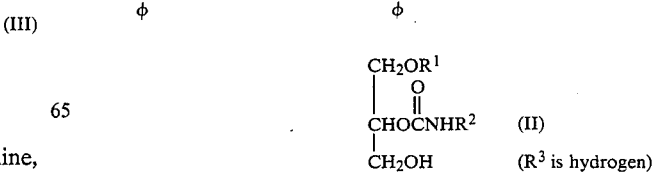 (II)

($R^3$ is hydrogen)

-continued

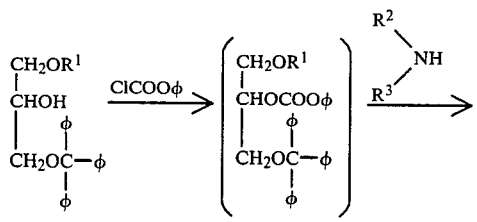 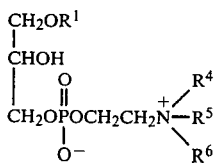

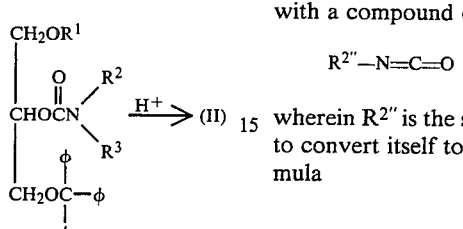

In the above formulae, $\phi$ represents phenyl and all the other symbols are as defined above.

Process B

A compound (I) can be produced by reacting the compound (II) with a compound of the formula

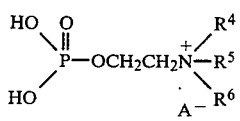 (VII)

wherein all symbols are as defined above, with the aid of a phosphate activating reagent.

Process C

A phosphorylating agent is allowed to act on a compound of the formula (II) to give a compound of the formula

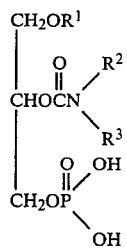 (VIII)

wherein all symbols are as defined above, and, then, the compound (VIII) is converted to a reactive derivative thereof. This reactive derivative is reacted with a compound of the formula

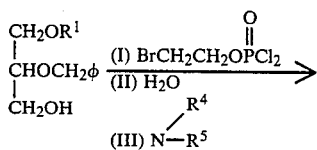 (IX)

wherein all symbols are as defined above, to give the compound (I).

Process D

A compound of the formula

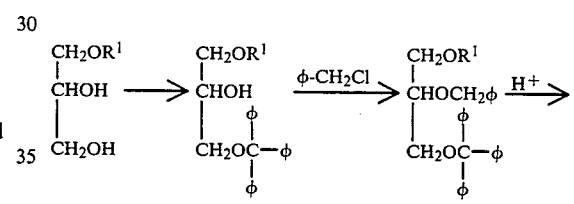 (X)

wherein all symbols are as defined above, is reacted with a compound of the formula $$R^{2''}-N=C=O \qquad (XI)$$

wherein $R^{2''}$ is the same as $R^2$ or a group which is ready to convert itself to $R^2$, or with a compound of the formula

 (XII)

wherein all symbols are as defined above, to give the compound (I).

In the above process, the compound of the formula (X) can be produced, for example, by the following process.

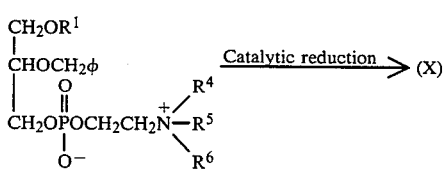

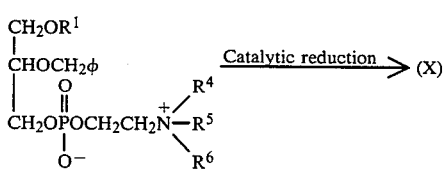

In the above formulae, all symbols are as defined above.

The above compound (I') can be produced, for example, by the following processes.

Process A'

A compound of the formula

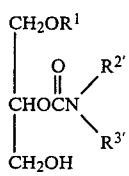 (II')

wherein all symbols are as defined above, is reacted with the compound (III) to give a compound of the formula $$\begin{array}{l} CH_2OR^1 \\ | \\ CHOCN\overset{O}{\underset{\|}{}}\begin{array}{l}R^{2'}\\ \diagup \\ \diagdown \\ R^{3'}\end{array} \\ | \\ CH_2O\overset{O}{\underset{\|}{P}}OCH_2CH_2Y \\ | \\ Z \end{array} \quad (IV')$$

wherein all symbols are as defined above. Then water is allowed to act on the compound (IV') to give a compound of the formula $$\begin{array}{l} CH_2OR^1 \\ | \\ CHOCN\overset{O}{\underset{\|}{}}\begin{array}{l}R^{2'}\\ \diagup \\ \diagdown \\ R^{3'}\end{array} \\ | \\ CH_2O\overset{O}{\underset{\|}{P}}OCH_2CH_2Y \\ | \\ OH \end{array} \quad (V')$$

wherein all symbols are as defined above.

The compound (V') can also be produced by converting the compound (IIIa), to an active derivative thereof and, then, reacting the latter with the compound (II').

Reacting the compound (V') with a compound of the formula $$\begin{array}{l}\phantom{N}\diagup R^{4'} \\ N-R^{5'} \\ \phantom{N}\diagdown R^{6'}\end{array} \quad (VI')$$

wherein all symbols are as defined above, gives a compound of the formula (I')

The compound (II') can be produced, for example, by the following processes.

$$\begin{array}{l} CH_2OR^1 \\ | \\ CHOH \\ | \\ CH_2OC-\phi \\ \phantom{CH_2O}| \\ \phantom{CH_2OC}\phi \end{array} \xrightarrow{R^{2'}N=C=O} \begin{array}{l} CH_2OR^1 \\ | \\ CHOCNHR^{2'} \\ \phantom{CH}| \\ CH_2OC-\phi \\ \phantom{CH_2O}| \\ \phantom{CH_2OC}\phi \end{array} \xrightarrow{H^+}$$

$$\begin{array}{l} CH_2OR^1 \\ | \\ CHOCNHR^{2'} \\ | \\ CH_2OH \end{array} \quad (II') \quad (R^{3'} \text{ is hydrogen})$$

$$\begin{array}{l} CH_2OR^1 \\ | \\ CHOH \\ | \\ CH_2OC-\phi \\ \phantom{CH_2O}| \\ \phantom{CH_2OC}\phi \end{array} \xrightarrow{ClCOO\phi} \left[\begin{array}{l} CH_2OR^1 \\ | \\ CHOCOO\phi \\ | \\ CH_2OC-\phi \\ \phantom{CH_2O}| \\ \phantom{CH_2OC}\phi \end{array}\right] \xrightarrow{\begin{array}{l}R^{2'}\\ \diagdown \\ NH \\ \diagup \\ R^{3'}\end{array}}$$

-continued $$\begin{array}{l} CH_2OR^1 \\ | \\ CHOCN\overset{O}{\underset{\|}{}}\begin{array}{l}R^{2'}\\ \diagup \\ \diagdown \\ R^{3'}\end{array} \\ | \\ CH_2OC-\phi \\ \phantom{CH_2O}| \\ \phantom{CH_2OC}\phi \end{array} \xrightarrow{H^+} (II')$$

In the above formulae, $\phi$ represents phenyl and all the other symbols are as defined above.

Process B'

A compound (I') can be produced by reacting the compound (II') with a compound of the formula $$\begin{array}{l} HO\diagdown\overset{O}{\underset{\|}{}}\phantom{OCH_2CH_2N}\diagup R^{4'} \\ \phantom{HO}P-OCH_2CH_2\overset{+}{N}-R^{5'} \\ HO\diagup\phantom{OCH_2CH_2N}\diagdown R^{6'} \\ \phantom{HO}\phantom{P-OCH_2CH_2N}A^- \end{array} \quad (VII')$$

wherein all symbols are as defined above, with the aid of a phosphate activating reagent.

Process C'

A phosphorylating agent is allowed to act on a compound of the formula (II') to give a compound of the formula $$\begin{array}{l} CH_2OR^1 \\ | \\ CHOCN\overset{O}{\underset{\|}{}}\begin{array}{l}R^{2'}\\ \diagup \\ \diagdown \\ R^{3'}\end{array} \\ | \\ CH_2O\overset{O}{\underset{\|}{P}}\begin{array}{l}OH \\ \diagup \\ \diagdown \\ OH\end{array} \end{array} \quad (VIII')$$

wherein all symbols are as defined above, and, then, the compound (VIII') is converted to a reactive derivative thereof. This reactive derivative is reacted with a compound of the formula $$\begin{array}{l} \phantom{HOCH_2CH_2N}\diagup R^{4'} \\ HOCH_2CH_2\overset{+}{N}-R^{5'} \\ \phantom{HOCH_2CH_2N}\diagdown R^{6'} \\ \phantom{HOCH_2CH_2N}A^- \end{array} \quad (IX')$$

wherein all symbols are as defined above, to give the compound (I').

Process D'

A compound of the formula $$\begin{array}{l} CH_2OR^1 \\ | \\ CHOH \\ | \\ CH_2O\overset{O}{\underset{\|}{P}}OCH_2CH_2\overset{+}{N}\begin{array}{l}R^{4'} \\ \diagup \\ \diagdown \\ R^{6'}\end{array} \\ \phantom{CH_2OP}| \\ \phantom{CH_2OP}O^- \phantom{CH_2N}R^{5'} \end{array} \quad (X')$$

wherein all symbols are as defined above, is reacted with a compound of the formula $$R^{2'''}-N=C=O \quad (XI')$$

wherein $R^{2'''}$ is the same as $R^{2'}$ or a group which is ready to convert itself to $R^{2'}$, or with a compound of the formula

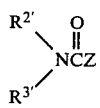
(XII')

wherein all symbols are as defined above, to give the compound (I').

In the above process, the compound of the formula (X') can be produced, for example, by the following process.

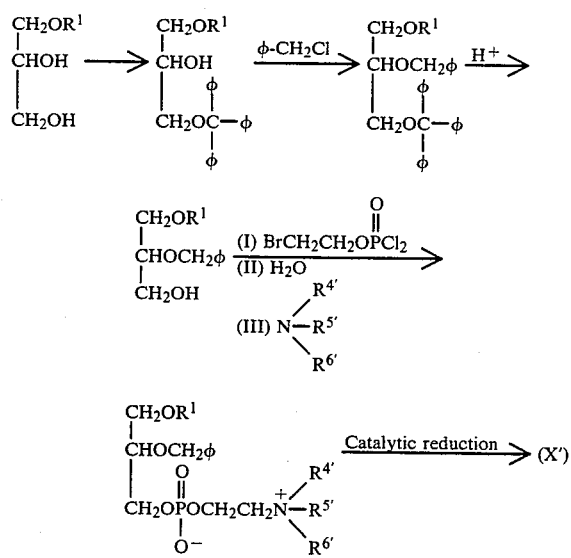

In the above formulae, all symbols are as defined above.

The representative processes for producing the compounds (I) and (I') are described above but the compounds (I) and (I') can also be produced by means of proper combinations of other known reactions and reaction routes.

There are two stereoisomers respectively of the compounds (I) and (I'), i.e. R-configurated and S-configurated, and this invention encompasses these respective isomers and a mixture thereof.

The glycerol derivatives of the formulae (I) and (I'), and salts thereof exhibit notable hypotensive activities in animals, in particular, in mammals and are useful, for example, as hypotensive drugs for prevention or treatment of hypertension. The compounds (I), (I') and salts thereof are well absorbed even by oral administration and display highly desirable effects at low dose levels so that they are very safe drugs. When they are used as the above-mentioned drugs, they can safely be administered orally or parenterally, per se in a form of pharmaceutical composition. While the dosage level generally varies depending upon the conditions of the diseases to be treated as well as the administration route used, for example, in the treatment of hypertension in adult human, the compounds may be administered orally at a single dose of about 0.02–5 mg/kg, preferably about 0.2–2 mg/kg. This dose is administered preferably about once or three times per day, depending on the conditions of patients.

The pharmaceutical compositions used as hypotensive drugs contain an effective amount of the compounds (I) and (I') or salts thereof as an active ingredient and a pharmaceutically acceptable carrier or excipient therefor. These compositions are made available in various dosage forms suitable for oral or parenteral administration.

Thus, the compositions include solid or liquid forms, specifically in such dosage forms as tablets (inclusive of sugar-coated tablets and film-coated tablets), pills, granules, powders, capsules (inclusive of soft capsules), syrups, emulsions, suspensions, etc. Such compositions can be prepared by the known procedures and contain carriers or excipients which are usually used in pharmaceutical practice. For example, the carrier or excipient for tablets include lactose, starch, sucrose, magnesium stearate, etc.

The compositions for parenteral administration include injections, suppositories, etc. and the preparations of the injections include intravenous or intramuscular injections and the like. Such injections can be prepared by the well-known methods, i.e. by dissolving, suspending or emulsifying the compounds (I) and (I') or salts thereof in a sterile aqueous or oleaginous medium which is conventionally used in the preparation of injections. The aqueous medium for injections include physiological saline solution and isotonic solutions, etc., and if necessary, the medium may be employed together with such suitable solubilizing agents as alcohols (e.g. ethanol), polyalcohols (e.g. propylene glycol, polyethylene glycol), nonionic surfactants [e.g. polysorbate 80, HCO-50 (polyoxyethylene (50 mol) adduct of hydrogenated castor oil)] etc. The oleaginous medium includes sesame oil, soybean oil or the like, and may be employed together with the solubilizing agents such as benzyl benzoate, benzyl alcohol, etc. The prepared injective solutions are generally filled in suitable ampules. The suppositories for rectal administration are prepared by mixing the compounds (I) or (I') or salts thereof with an ordinary suppository base.

The above-mentioned oral or parenteral pharmaceutical compositions are preferably made available in unit dosage forms corresponding to the required dose of the active ingredient. Such unit dosage forms include tablets, pills, capsules, injections (ampules), suppositories, etc. Usually 1 to 50 mg of the compound (I) or (I') is contained in a unit dosage form, preferably 1 to 10 mg in the case of injections and 1 to 25 mg in the case of other dosage forms.

Each of the above-mentioned compositions may further contain other active ingredients unless they do not undergo untoward interactions with the compound (I) or (I').

The invention will be further illustrated in more detail by the following embodiment examples, test examples and dosage form examples, which, however, are by no means limitative of the present invention.

EXAMPLE 1

1-Octadecyl-sn-glycerol

According to the procedure of the reference [FEBS Letters, Vol. 116, 161 (1980)], D-mannitol was used as a starting material to give 25 g of the desired compound (needles) through 1,2-isopropylidene-sn-glycerol.

EXAMPLE 2

1-Octadecyl-3-trityl-sn-glycerol

1-Octadecyl-sn-glycerol (11.0 g, 31.9 mmol) and 17.8 g (63.8 mmol) of trityl chloride were dissolved in 95 ml of pyridine. The solution was stirred at 30° C. overnight and then concentrated to dryness under reduced pressure. The residue was dissolved in 200 ml of dichloromethane, and the solution was washed with 25% acetic acid, water and 5% sodium hydrogen carbonate in that order. The organic layer was dried over sodium sulfate and concentrated to dryness under reduced pressure, and the residue was dissolved in 100 ml of petroleum ether while hot. After cooling, the insoluble material was filtered off and the filtrate was concentrated to dryness under reduced pressure to give the above-identified compound as a colorless solid. Yield 17.6 g (94.0%).

Thin-layer chromatography [silica gel, n-hexane-acetic acid (4:1)]: Rf=0.75, single spot.

NMR (60 MHz, CDCl$_3$) δ: 1.7–0.8(36H), 3.63–3.17(7H), 3.97(1H), 7.4(15H).

EXAMPLE 3

2-Benzyl-1-octadecyl-sn-glycerol

1-Octadecyl-3-trityl-sn-glycerol (17.0 g, 24.5 mmol) and 10.8 g (85.4 mmol) of benzyl chloride were dissolved in 57 ml of dimethyl sulfoxide, and 8.0 g of powdered potassium hydroxide was added. The mixture was stirred vigorously at room temperature for 3 hours, then poured into 570 ml of ice water, neutralized with concentrated hydrochloric acid, and extracted with 600 ml of ether. The organic layer was dried over sodium sulfate and concentrated to dryness under reduced pressure. To the residue was added 300 ml of 80% acetic acid, and the mixture was stirred at 60° C. for 3 hours and concentrated to dryness under reduced pressure. The residue was purified by column chromatography on silica gel (150 g) using n-hexane-ethyl acetate (10:1) as the eluent to give the above-identified compound as a colorless solid.

Yield 9.2 g (86.4%).

Thin-layer chromatography [silica gel, n-hexane-ethyl acetate (4:1)]: Rf=0.24, single spot.

NMR (60 MHz, CDCl$_3$) δ: 0.73–1.77(35H), 3.17–3.67(7H), 4.50(1H), 4.67(2H), 7.40(5H).

EXAMPLE 4

(2R)-2-Benzyloxy-3-octadecyloxypropyl 2-bromoethyl phosphate

1-Octadecyl-2-benzyl-sn-glycerol (4.0 g, 9.5 mmol) and 3.44 g (14.2 mmol) of 2-bromoethyl phosphorodichloridate were dissolved in 20 ml of benzene, and 1.12 g of pyridine was added dropwise. The mixture was stirred at room temperature for 4 hours and concentrated to dryness under reduced pressure. To the residue was added 20 ml of water, and the mixture was refluxed for 30 minutes, cooled and extracted with 70 ml of dichloromethane. The organic layer was concentrated to dryness under reduced pressure. Yield 5.5 g (93.3%).

Thin-layer chromatography [silica gel, chloroform-methanol-water (65:25:4)]: Rf=0.65, single spot.

EXAMPLE 5

(2R)-2-Benzyloxy-3-octadecyloxypropyl 2-trimethylammonioethyl phosphate

The bromide compound (5.5 g, 8.86 mmol) obtained in Example 4 was dissolved in 100 ml of 20% trimethylamine-in-toluene, and the solution was allowed to stand at room temperature for 3 days and then concentrated to dryness under reduced pressure. The residue was dissolved in 50 ml of methanol and 5.0 g of silver carbonate was added. The mixture was refluxed for 30 minutes and the insoluble material was filtered off. The filtrate was concentrated to dryness under reduced pressure and the residue was purified by column chromatography on silica gel (55 g) using methanol as the eluent to give the above-identified compound as a colorless solid. Yield 4.0 g (75.0%).

$[\alpha]_D^{22}$ = +3.8° (c=1, CHCl$_3$).

NMR (60 MHz, CDCl$_3$) δ: 0.93(3H), 1.27(32H), 3.22(9H), 3.4–4.5(11H), 4.75(2H) 7.40(5H).

IR(film)cm$^{-1}$: 3400, 2920, 2855, 1465, 1240, 1090, 1060.

EXAMPLE 6

(2R)-2-Hydroxy-3-octadecyloxypropyl 2-trimethylammonioethyl phosphate

The benzyl compound (3.5 g, 5.83 mmol) obtained in Example 5 was dissolved in 70 ml of 70% acetic acid and hydrogenated on 350 mg of palladium-on-carbon for 3 hours. The catalyst was filtered off and the filtrate was concentrated to dryness under reduced pressure. The residue was purified by column chromatography on silica gel (25 g) using chloroform-methanol-water (65:25:4) as the eluent to give a colorless powder. Yield 3.4 g (100%).

$[\alpha]_D^{22}$ = −4.8° (c=1, CHCl$_3$).

NMR (100 MHz, CD$_3$OD) δ: 0.90(3H), 1.30(30H), 1.56(2H), 3.23(9H), 3.30(4H), 3.46(2H), 3.64(1H), 3.86(2H), 4.28(2H).

IR(KBr)cm$^{-1}$: 3420, 2920, 2850, 1465, 1230, 1085, 1055.

EXAMPLE 7

(2S)-2-Hydroxy-3-octadecyloxypropyl 2-trimethylammonioethyl phosphate

In accordance with the process in Examples 2–6, using 3-octadecyl-sn-glycerol described in Example 1 as the starting compound, there was obtained 1.5 g of the above-identified compound as a colorless powder.

$[\alpha]_D^{22}$ = +4.9° (c=1, CHCl$_3$).

IR(KBr) cm$^{-1}$: 3420, 2920, 2850, 1465, 1230, 1085, 1055.

EXAMPLE 8

(2R)-2-Benzyloxy-2-octadecyloxypropyl 2-pyridinioethyl phosphate

The bromide compound (1.86 g, 3.0 mmol) obtained in Example 4 was dissolved in 6 ml of pyridine, and the solution was heated at 50° C. for 3 days and then concentrated to dryness under reduced pressure. The residue was dissolved in 10 ml of methanol and 1.0 g of silver carbonate was added. The mixture was stirred at room temperature for 2 hours and the insoluble material was filtered off. The filtrate was concentrated to dryness under reduced pressure and the residue was purified by column chromatography on silica gel (10 g)

using methanol as the eluent to give the above-identified compound as a colorless syrup. Yield 0.6 g (32.3%).

Thin-layer chromatography [silica gel, chloroform-methanol-water (65:25:4)]: Rf=0.39, single spot.

NMR (60 MHz, CDCl$_3$) δ: 0.93(3H), 1.27(32H), 3.0–4.6(11H), 4.73(2H), 7.40(5H), 8.3(2H), 8.75(1H), 9.10(2H).

EXAMPLE 9

(2R)-2-Hydroxy-3-octadecyloxypropyl 2-pyridinioethyl phosphate

The benzyl compound (600 mg, 1.02 mmol) obtained in Example 8 was dissolved in 20 ml of 70% acetic acid and hydrogenated on palladium-on-carbon for 4 hours. The insoluble material was filtered off and the filtrate was concentrated to dryness under reduced pressure. The residue was purified by column chromatography on silica gel (1 g) using chloroform-methanol-water (65:25:4) as the eluent to give 340 mg (66.8%) of the above-identified compound as a colorless powder.

Thin-layer chromatography [silica gel, chloroform-methanol-water (32:25:4)]: Rf=0.21, single spot.

NMR (60 MHz, CDCl$_3$) δ: 0.77(3H), 1.26(32H), 3.3–3.6(11H), 3.77(2H), 4.33(2H), 8.30(2H), 8.77(1H); 9.13(2H).

EXAMPLE 10

2-(N,N-Dimethylcarbamoyl)-1,3-benzylideneglycerol 1,3-benzylideneglycerol (360 mg, 2 mmol) and pyridine (316 mg, 3 mmol) were dissolved in 4 ml of dichloromethane, and phenyl chlorocarbonate (313 mg, 2 mmol) was added dropwise. The mixture was stirred at room temperature for an hour and 10 ml of chloroform and 10 ml of water were added. The resulting mixture was stirred for a while. The organic layer was separated and the aqueous layer was discarded. The organic layer was concentrated to dryness under reduced pressure and the residue was dissolved in 2 ml of dichloromethane. The solution was stirred for an hour, which dimethylamine gas being bubbled thereinto and then the reaction mixture was concentrated to dryness under reduced pressure. The residue was recrystallized from hot methanol to give 470 mg (93.5%) of the above-identified compound as colorless needles, melting at 117°–120° C.

Thin-layer chromatography [silica gel, n-hexane-ethyl acetate (1:1)]: Rf=0.40, single spot.

NMR (60 MHz, CDCl$_3$) δ: 2.97(6H), 3.73–4.50(4H), 4.58(1H), 5.50(1H), 7.33(5H).

EXAMPLE 11

2-(N,N-Dimethylcarbamoyl)glycerol

The 1,3-benzylidene compound (450 mg, 1.79 mmol) obtained in Example 10 was dissolved in a mixture of 4 ml of methanol and 0.04 ml of concentrated hydrochloric acid. The solution was refluxed for an hour and then concentrated to dryness under reduced pressure. Water (4 ml) was added and the mixture was concentrated to dryness to remove benzaldehyde. This treatment was repeated twice and the residue was dried over P$_2$O$_5$. Yield 292 mg (100%).

NMR (60 MHz, CDCl$_3$) δ: 2.92(6H), 3.73(4H), 4.08(2H), 4.77(1H).

EXAMPLE 12

2-(N,N-Dimethylcarbamoyloxy)-3-(N-octadecylcarbamoyloxy)-1-propanol

The propanol compound (2.6 g 15.92 mmol) obtained in Example 11 and 4.43 g of octadecyl isocyanate were dissolved in 40 ml of dichloromethane. The solution was stirred at room temperature overnight and then concentrated to dryness under reduced pressure. The residue was purified by column chromatography on silica gel (60 g) using n-hexane-ethyl acetate (1:1) as the eluent to give the above-identified compound as a colorless solid. Yield 1.77 g (23.7%).

EXAMPLE 13

2-(N,N-Dimethylcarbamoyloxy)-3-(N-octadecylcarbamoyloxy)-propyl 2-bromoethyl phosphate The alcohol compound (1.77 g, 3.78 mmol) obtained in Example 12 and 1.37 g (5.67 mmol) of 2-bromoethyl-phosphorodichloridate were dissolved in 7.2 ml of benzene, and 0.448 g (5.67 mmol) of pyridine was added dropwise. The mixture was stirred at room temperature for 5 hours, followed by addition of 7.2 ml of water. The resulting mixture was stirred vigorously overnight and then shaken with 20 ml of chloroform and 20 ml of water. The organic layer was separated and the aqueous layer was discarded. The organic layer was concentrated to dryness under reduced pressure to give the above-identified compound as a colorless solid. Yield 2.4 g (100%).

EXAMPLE 14

2-(N,N-Dimethylcarbamoyloxy)-3-(N-octadecylcabamoyloxy)-propyl 2-trimethylammonioethyl phosphate The bromide compound (1.2 g, 1.89 mmol) obtained in Example 13 was dissolved in 20 ml of 20% trimethylamine-in-toluene. The solution was stirred in a sealed tube at room temperature for 3 days and then concentrated to dryness under reduced pressure. The residue was treated with silver carbonate and purified by column chromatography on silica gel (8 g) using methanol as the eluent to give the above-identified compound as a colorless solid. Yield 729 mg (61.8%)

Thin-layer chromatography [silica gel, chloroform-methanol-water (65:25:4)]: Rf=0.12, single spot.

IR(film)cm$^{31\ 1}$: 3350, 2920, 2850, 1690, 1530, 1460, 1400, 1240, 1090, 1080, 1050.

NMR (60 MHz, CDCl$_3$) δ: 0.88(3H), 1.27(32H), 2.88(6H), 3.13(2H), 3.35(9H), 3.63–4.67(8H), 5.00(1H), 5.67(1H).

EXAMPLE 15

2-(N,N-Dimethylcarbamoyloxy)-3-(N-octadecylcarbamoyloxy)-propyl 2-pyridinioethyl phosphate The bromide compound (1.2 g, 1.89 mmol) obtained in Example 13 was dissolved in 20 ml of pyridine. The solution was stirred at 50° C. overnight, then refluxed for an hour and concentrated to dryness under reduced pressure. The residue was treated with silver carbonate in methanol and purified by column chromatography on silica gel (8 g) using methanol as the eluent to give a light-brown solid.

Yield 326 mg (26.8%).

Thin-layer chromatography [silica gel, chloroform-methanol-water (65:25:4)]: Rf=0.18, single spot.

IR(film)cm$^{-1}$: 3350, 2920, 2850, 1695, 1530, 1490, 1460, 1240, 1190, 1070, 1050(sh).

NMR (60 MHz, CDCl$_3$) δ: 0.88(3H), 1.25(32H), 2.88(6H), 3.23(2H), 3.33–4.67(6H), 5.05(3H), 5.75(1H), 8.10(2H), 8.43(1H), 9.42(2H).

EXAMPLE 16

2-(N,N-Dimethylcarbamoyl)-3-octadecyl-1-tritylglycerol

3-Octadecyl-1-tritylglycerol (2.6 g, 4.43 mmol) and 0.7 g (8.86 mmol) of pyridine were dissolved in 9 ml of dichloromethane, and 0.69 g of phenyl chlorocarbonate was added dropwise. The solution was stirred at room temperature for 30 minutes, and then stirred with 25 ml of chloroform and 25 ml of water. The aqueous layer was discarded and the organic layer was washed with 1% sodium hydrogen carbonate solution, dried over sodium sulfate and concentrated to dryness under reduced pressure. The residue was dissolved in 13 ml of dichloromethane, and dimethylamine gas was bubbled into the solution. The solution was concentrated to dryness under reduced pressure and the residue was purified by column chromatography on silica gel (20 g) using n-hexane-ethyl acetate (9:1) as the eluent to give 2.92 g (100%) of colorless needles, melting at 57.5°–58.0° C.

NMR (60 MHz, CDCl$_3$) δ: 0.88(3H), 1.27(32H), 2.92(2H), 3.37(2H), 3.60(2H), 5.07(1H), 7.25(15H).

EXAMPLE 17

2-(N,N-Dimethylcarbamoyl)-3-octadecylglycerol

The trityl compound (2.92 g, 4.43 mmol) obtained in Example 16 was added to 29 ml of 80% acetic acid and the mixture was stirred at 100° C. for an hour and then concentrated to dryness under reduced pressure. The residue was purified by column chromatography on silica gel (13 g) using n-hexane-ethyl acetate (4:1) as the eluent to give the above-identified compound as a colorless solid.

Yield 1.6 g (86.9%).

Thin-layer chromatography [silica gel, chloroform-methanol (19:1)]: Rf=0.60, single spot.

NMR (60 MHz, CDCl$_3$)δ: 0.87(3H), 1.25(32H), 2.92(6H), 3.43(2H), 3.58(2H), 3.77(2H), 4.83(1H).

EXAMPLE 18

2-(N,N-Dimethylcarbamoyloxy)-3-octadecyloxypropyl 2-bromoethyl phosphate

The alcohol compound (1.6 g, 3.84 mmol) obtained in Example 17 was treated in the same manner as Examples 4 and 13 to give 2.32 g (100%) of the above-identified compound as a solid.

EXAMPLE 19

2-(N,N-Dimethylcarbamoyloxy)-3-octadecyloxypropyl 2-trimethylammonioethyl phosphate The bromide compound (773 mg, 1.28 mmol) obtained in Example 18 was treated in 20% trimethylamine-in-toluene in the same manner as Examples 5 and 14 to give the above-identified compound as a colorless solid. Yield 250 mg (33.6%).

IR(film)cm$^{-1}$: 3390, 2920, 2850, 1690, 1490, 1465, 1400, 1230, 1190, 1085, 1060, 970.

NMR (60 MHz, CDCl$_3$) δ: 0.88(3H), 1.27(32H), 2.90(6H), 3.38(9H), 3.4–4.10(8H), 4.28(2H), 4.98(1H).

Thin-layer chromatography [silica gel, chloroform-methanol-water (65:25:4)]: Rf=0.13, single spot.

EXAMPLE 20

2-(N,N-Dimethylcarbamoyloxy)-3-octadecyloxypropyl 2-pyridinioethyl phosphate

The bromide compound (773 mg, 1.28 mmol) obtained in Example 18 was dissolved in 20 ml of pyridine, and the reaction was allowed to proceed at 60° C. for 3 days. The reaction mixture was treated in the same manner as Examples 8 and 15 to give the above-identified compound as a colorless solid. Yield 133 mg (17.3%).

Thin-layer chromatography [silica gel, chloroform-methanol-water (65:25:4)]: Rf=0.14, single spot.

IR(film)cm$^{-1}$: 3400, 2930, 2850, 1690, 1490, 1460, 1400, 1240, 1195, 1095, 1070, 1055, 930.

NMR (60 MHz, CDCl$_3$) δ: 0.88(3H), 1.25(32H), 2.87(6H), 3.2–3.7(4H), 3.91(2H), 4.30(2H), 4.97(3H), 8.00(2H), 8.38(1H), 9.30(2H).

EXAMPLE 21

2-N,N-Dimethylcarbamoyloxy)-3-octadecyloxypropyl 2-thiazolioethyl phosphate

The bromide compound (773 mg, 1.28 mmol) obtained in Example 18 was dissolved in 2 ml of thiazole. The solution was heated at 60° C. for 3 days and then concentrated to dryness under reduced pressure. The residue was dissolved in 20 ml of methanol, and 500 mg of silver carbonate was added. The mixture was stirred at room temperature for an hour. By column chromatography on silica gel (7 g) using methanol as the eluent was obtained the above-identified compound as a colorless solid.

Yield 95 mg (12.2%).

Thin-layer chromatography [silica gel, chloroform-methanol-water (65:25:4)]: Rf=0.18, single spot.

IR(film)cm$^{-1}$: 3490, 2920, 2850, 1690, 1490, 1460, 1240, 1195, 1090, 1060.

NMR (60 MHz, CDCl$_3$) δ:0.88(3H), 1.25(32H), 2.88(6H), 3.2–3.7(4H), 3.93(2H), 4.28(2H), 4.88(3H), 8.25(1H), 8.53(1H), 10.62(1H).

EXAMPLE 22

2-(N-Methylcarbamoyl)-1-octadecylglycerol

1-Octadecyl-3-tritylglycerol (2.6 g, 4.43 mmol) and 3 ml of methyl isocyanate were dissolved in 10 ml of pyridine, and the solution was heated at 60° C. for 12 hours and then concentrated to dryness under reduced pressure. To the residue was added 50 ml of 80% acetic acid and the mixture was stirred at 100° C. for 1.5 hours and then concentrated to dryness under reduced pressure. The residue was purified by column chromatography on silica gel (20 g) using n-hexane-ethyl acetate (2:1) as the eluent to give the above-identified compound as a colorless solid.

Yield 1.45 g (81.5%).

Thin-layer chromatography [silica gel, chloroform-methanol (19:1)]: Rf=0.34, single spot.

NMR (60 MHz, CDCl$_3$) δ: 0.88(3H), 1.26(32H), 2.61(3H), 3.42(2H), 3.58(2H), 3.75(2H), 4.80(1H), 5.50(1H).

EXAMPLE 23

2-(N-Methylcarbamoyloxy)-3-octadecyloxypropyl 2-bromoethyl phosphate

The alcohol compound obtained in Example 22 was treated in the same manner as Example 4 and 13 to give the above-identified compound as a colorless solid. Yield 2.15 g (100%).

Thin-layer chromatography [chloroform-methanol-water (65:25:4)]: Rf=0.41.

EXAMPLE 24

2-(N-Methylcarbamoyloxy)-3-octadecyloxypropyl 2-pyridinioethyl phosphate

The bromide compound (531 mg, 0.9 mmol) obtained in Example 23 was treated in the same manner as Examples 8 and 15 to give the above-identified compound as a colorless solid. Yield 175 mg (33.1%).

Thin-layer chromatography [silica gel, chloroform-methanol-water (65:25:4)]: Rf=0.15, single spot.

IR(film)cm$^{-1}$: 3370, 3050, 2920, 2850, 1705, 1525, 1495, 1460, 1240, 1225, 1205, 1140, 1090, 1075, 1050, 930, 815, 650.

NMR (60 MHz, CDCl$_3$) δ: 0.88(3H), 1.28(32H), 2.63(3H), 3.17–4.0(6H), 4.30(2H), 4.96(3H), 6.83(1H), 8.00(2H), 8.40(1H), 9.23(2H).

EXAMPLE 25

2-(N-Methylcarbamoyloxy)-3-octadecyloxypropyl 2-thiazolioethyl phosphate

The bromide compound (531 mg, 0.903 mmol) obtained in Example 23 was dissolved in 2 ml of thiazole, and the solution was heated at 60° C. for 3 days. It was then treated in the same manner as Example 21 to give 88 mg (16.4%) of the above-identified compound as a colorless solid.

Thin-layer chromatography [silica gel, chloroform-methanol-water (65:25:4)]: Rf=0.14, single spot.

IR(film)cm$^{-1}$: 3350, 2920, 2850, 1700, 1560, 1460, 1240, 1090, 1060.

EXAMPLE 26

2-(N-Methylcarbamoyloxy)-3-octadecyloxypropyl 2-morpholinoethyl phosphate

The bromide compound (531 mg, 0.9 mmol) obtained in Example 23 was dissolved in 2 ml of morpholine. The solution was heated at 60° C. for 3 days and then concentrated to dryness under reduced pressure. The residue was dissolved in 20 ml of methanol and 400 mg of silver carbonate was added. The mixture was stirred at room temperature for an hour and the insoluble material was filtered off. A small amount of hydrogen sulfide was bubbled into the filtrate and the resulting insoluble material was filtered off. The filtrate was concentrated to dryness under reduced pressure and the residue was purified by column chromatography on silica gel using methanol as the eluent to give the above-identified compound as a colorless solid. Yield 105 mg (19.1%).

Thin-layer chromatography [chloroform-methanol-water (65:25:4)]: Rf=0.33, single spot.

IR(film)cm$^{-1}$: 3350, 2910, 2850, 1700, 1540, 1460, 1250, 1110, 1060, 950, 850.

NMR (60 MHz, CDCl$_3$) δ: 0.88(3H), 1.27(32H), 2.70(9H), 3.2–4.4(12H), 5.05(1H), 6.27(1H).

Elemental analysis for C$_{29}$H$_{59}$N$_2$O$_8$P.H$_2$O

Calcd.: C, 56.84; H, 10.03; N, 4.57. Found: C, B 56.79; H, 9.39; N, 4.60.

EXAMPLE 27

2-Benzyloxy-3-octadecylcarbamoyloxypropyl 2-trimethylammonioethyl phosphate

1-Octadecylcarbamoyl-2-benzylglycerol (1.7 g) and 1.31 g of 2-bromoethyl phosphorodichloridate were dissolved in 25 ml of benzene, and 0.44 g of pyridine was added dropwise. The mixture was stirred at room temperature for 1.5 hours and the benzene was then distilled off. Water (25 ml) was added and the mixture was refluxed for 45 minutes. After cooling, the reaction mixture was extracted with chloroform, and the extract was washed water, dried and concentrated. To the residue was added 25 ml of trimethylamine-in-toluene and the mixture was allowed to stand at room temperature for 4 days. The solvent was then distilled off, and 2.0 g of silver carbonate and then 25 ml of methanol were added to the residue. The mixture was refluxed for an hour and the insoluble material was filtered off. The filtrate was concentrated to dryness and the residue was purified by silica gel column chromatography using methanol as the eluent to give 1.4 g of the above-identified compound.

NMR (60 MHz, CDCl$_3$) δ: 0.87(3H), 1.20(32H), 3.06(9H), 3.3–4.5(11H), 4.54(2H), 7.20(5H).

EXAMPLE 28

2-Hydroxy-3-octadecylcarbamoyloxypropyl 2-trimethylammonioethyl phosphate

The benzyl compound (1.4 g) obtained in Example 27 was dissolved in 50 ml of acetic acid and hydrogenated on 100 mg of palladium-on-carbon. Then, the catalyst was removed and the filtrate was concentrated to dryness. The residue was purified by column chromatography on silica gel (15 g) using chloroform-methanol-water (65:25:4) as the eluent to give the above-identified compound.

EXAMPLE 29

2-Methylcarbamoyloxy-3-octadecylcarbamoyloxypropyl 2-trimethylammonioethyl phosphate The hydroxy compound (300 mg) obtained in Example 28 and 1.5 ml of methyl isocyanate were dissolved in 7 ml of pyridine, and the solution was warmed at 50° C. for 5 hours. The solvent was then distilled off and the residue was purified by silica gel column chromatography [silica gel: 10 g; eluent: chloroform-methanol-water (65:25:4)] to give 298 mg of the above-identified compound.

NMR (60 MHz, CDCl$_3$) δ: 0.87(3H), 1.23(32H), 2.73(3H), 3.33(9H), 3.0–4.8(10H), 5.02(1H), 5.99(1H), 6.80(1H).

EXAMPLE 30

2-(N-n-Butylcarbamoyloxy)-3-octadecyloxy-1-propanol

A mixture of 2.6 g (4.43 mmol) of 3-octadecyl-1-tritylglycerol and 3 ml of n-butyl isocyanate in 5 ml of pyridine was heated at 80° C. for 6 hours, and the reaction mixture was concentrated to dryness under reduced pressure. To the residue was added 50 ml of 70% acetic acid, and the mixture was refluxed for 1.5 hours and then concentrated to dryness under reduced pressure. The residue was purified by column chromatography on silica gel (25 g) using n-hexane-ethyl acetate (4:1) as the eluent to give the above-identified compound as a colorless solid.

Thin-layer chromatography [silica gel, chloroform-methanol (19:1)]: Rf=0.59, single spot.

IR(film)cm$^{-1}$: 3330, 2920, 2850, 1695, 1530, 1465, 1250, 1110, 1050.

NMR (60 MHz, CDCl$_3$) δ: 0.92(6H), 1.27(36H), 2.62(1H), 3.0–4.0(8H), 4.83(1H), 7.50(1H).

EXAMPLE 31

2-(N-n-Butylcarbamoyloxy)-3-octadecyloxypropyl 2-bromoethyl phosphate

The alcohol compound (1.7 g, 3.83 mmol) obtained in Example 30 was treated in the same manner as Examples 4 and 13 to give a colorless solid. Yield 2.3 g (95.0%).

Thin-layer chromatography [silica gel, chloroform-methanol-water (65:25:4)]: Rf=0.64.

EXAMPLE 32

2-(N-n-Butylcarbamoyloxy)-3-octadecyloxypropyl 2-pyridinioethyl phosphate

The bromide compound (575 mg, 0.902 mmol) obtained in Example 31 was treated in the same manner as in Examples 8 and 15 to give a colorless solid. Yield 74.4 mg (12.0%).

Thin-layer chromatography [silica gel, chloroform-methanol-water (65:25:4)]: Rf=0.24, single spot.

IR(film)cm$^{-1}$: 3350, 2950, 2920, 2850, 1700, 1630, 1540, 1490, 1460, 1250, 1095, 1070, 1050(sh), 940, 760.

NMR (60 MHz, CDCl$_3$) δ: 0.88(6H), 1.27(36H), 3.07(2H), 3.30(2H), 3.43(2H), 3.80(2H), 4.38(2H), 5.00(3H), 6.52(1H), 8.03(2H), 8.33(1H), 9.43(2H).

EXAMPLE 33

2-(N-n-Butylcarbamoyloxy)-3-octadecyloxypropyl 2-thiazolioethyl phosphate

The bromide compound (1.15 g, 1.84 mmol) obtained in Example 31 was treated in the same manner as Example 21 to give a light-brown solid. Yield 189 mg (16.5%).

Thin-layer chromatography [silica gel, chloroform-methanol-water (65:25:4)]: Rf=0.24, single spot.

IR(film)cm$^{-1}$: 3350, 2920, 2850, 1700, 1540, 1470, 1245, 1095, 1060.

NMR (60 MHz, CDCl$_3$) δ: 0.90(6H), 1.27(36H), 3.13(2H), 3.50(4H), 3.55(2H), 4.27(2H), 4.97(3H), 6.20(1H), 8.27(1H), 8.60(1H), 10.70(1H).

EXAMPLE 34

3-Octadecyl-2-piperidinocarbonyl-1-tritylglycerol

The carbonate synthesized in the same manner as Example 16 from 2.6 g of 3-octadecyl-1-tritylglycerol, 0.7 g of pyridine, 0.69 g of phenyl chlorocarbonate and 9 ml of dichloromethane, was dissolved in 5 ml of piperidine. The solution was stirred at room temperature for an hour and then concentrated to dryness under reduced pressure. The residue was purified by silica gel column chromatography using n-hexane-ethyl acetate (9:1) as the eluent to give 3.09 g (100%) of the above-identified compound as a colorless oil.

Thin-layer chromatography [silica gel, n-hexane-ethyl acetate (4:1)]: Rf=0.61.

NMR (60 MHz, CDCl$_3$) δ: 0.90(3H), 1.27(32H), 1.55(6H), 3.19–3.72(10H), 5.12(1H), 7.10–7.61(15H).

IR(film)cm$^{-1}$: 1700, 1595.

EXAMPLE 35

3-Octadecyl-2-piperidinocarbonylglycerol

The trityl compound (3.09 g) obtained in Example 34 was dissolved in 30 ml of 80% acetic acid. The solution was stirred at 110° C. for 1.25 hours and then concentrated to dryness under reduced pressure. The residue was purified by silica gel column chromatography using n-hexane-ethyl acetate (4:1) as the eluent to give 1.50 g (74.4%) of the above-identified compound as a colorless oil.

Thin-layer chromatography [silica gel, n-hexane-ethyl acetate (4:1)]: Rf=0.13.

NMR (60 MHz, CDCl$_3$) δ: 0.89(3H), 1.28(32H), 1.58(6H), 3.25–3.91 (10H), 4.89(1H).

IR(film)cm$^{-1}$: 3450, 1680.

EXAMPLE 36

3-Octadecyloxy-2-(piperidinocarbonyloxy)propyl 2-trimethylammonioethyl phosphate The bromide compound synthesized in the same manner as Examples 4 and 13 from 750 mg of the alcohol compound obtained in Example 35, 598 mg of 2-bromoethyl phosphorodichloridate, 196 mg of pyridine and 8 ml of benzene, was dissolved in 15 ml of 20% trimethylamine-in-toluene. The solution was allowed to stand at room temperature for 84 hours and then treated in the same manner as Examples 5 and 14 to give 120 mg (11.7%) of the above-identified compound and a colorless solid.

Thin-layer chromatography [silica gel, chloroform-methanol-water (65:25:4)]: Rf=0.13.

NMR (60 MHz, CDCl$_3$) δ: 0.89(3H), 1.25(32H), 1.54(6H), 3.38(9H), 3.48–4.10(12H), 4.28(2H), 4.98(1H).

IR(film)cm$^{-1}$: 2920, 2850, 1690, 1230, 1090, 1060.

EXAMPLE 37

3-Octadecyloxy-2-(piperidinocarbonyloxy)propyl 2-dimethylaminoethyl phosphate

The bromide compound synthesized in the same manner as Examples 4 and 13 from 750 mg of the alcohol compound obtained in Example 35, 598 mg of 2-bromoethyl phosphorodichloridate, 196 mg of pyridine and 8 ml of benzene, was dissolved in 20 ml of 20% dimethylamine-in-toluene. The solution was allowed to stand at room temperature for 15.5 hours and then treated in the same manner as Examples 5 and 14 to give 178 mg (17.8%) of the above-identified compound as a colorless solid.

Thin-layer chromatography [silica gel, chloroform-methanol-water (65:25:4)]: Rf=0.48.

NMR (60 MHz, CDCl$_3$) δ: 0.89(3H), 1.27(32H), 1.54(6H), 2.58(6H), 3.14–4.32(14H), 5.00(1H).

IR(film)cm$^{-1}$: 2920, 2850, 1690, 1230, 1160, 1085.

EXAMPLE 38

2-(N,N-Dibutylcarbamoyl)-3-octadecyl-1-tritylglycerol

The carbonate compound synthesized in the same manner as Example 16 from 2.6 g of 3-octadecyl-1-tritylglycerol, 0.7 g of pyridine, 0.69 g of phenyl chlorocarbonate and 9 ml of dichloromethane, was dissolved in 5 ml of dibutylamine. The solution was stirred at 110° C. for 22 hours and concentrated to dryness under reduced pressure. The residue was dissolved in ether and washed with an aqueous solution of 5% hydrochloric acid and water. The organic layer was dried over anhydrous sodium sulfate and concentrated to dryness under reduced pressure. The residue was purified by silica gel column chromatography using n-hexane-ethyl acetate (9:1) as the eluent to give 2.73 g (83.2%) of the above-identified compound as a colorless oil.

Thin-layer chromatography [silica gel, n-hexane-ethyl acetate (9:1)]: Rf=0.35.

NMR (60 MHz, CDCl$_3$) δ: 0.89(9H), 1.30(32H), 1.40–1.75(8H), 2.86–3.75(10H), 5.11(1H), 7.02–7.58(15H).

IR(film)cm$^{-1}$: 1700, 1595.

EXAMPLE 39

2-(N,N-Dibutylcarbamoyl)-3-octadecylglycerol

The trityl compound (2.73 g) obtained in Example 38 was dissolved in 29 ml of 80% aqueous solution of acetic acid. The solution was stirred at 103° C. for 1.5 hours and concentrated to dryness under reduced pressure. The residue was purified by silica gel column chromatography using n-hexane-ethyl acetate (4:1) as the eluent to give 1.70 g (92.5%) of the above-identified compound as a colorless oil.

Thin-layer chromatography [silica gel, n-hexane-ethyl acetate (4:1)]: Rf=0.17.

NMR (60 MHz, CDCl$_3$) δ: 0.94(9H), 1.26(32H), 1.38–1.85(8H), 2.64–3.98(10H), 4.89(1H).

IR(film)cm$^{-1}$: 3470, 1680.

EXAMPLE 40

2-(N,N-Dibutylcarbamoyloxy)-3-octadecyloxypropyl 2-trimethylammonioethyl phosphate The bromide compound synthesized in the same manner as Examples 4 and 13 from 850 mg of the alcohol compound obtained in Example B 39, 618 mg of 2-bromoethyl phosphorodichloridate, 202 mg of pyridine and 7 ml of benzene, was dissolved in 15 ml of 20% trimethylamine-in-toluene. The solution was allowed to stand at room temperature for 48 hours and then treated in the same manner as Examples 5 and 14 to give 118 mg (10.4%) of the above-identified compound as a colorless syrup.

Thin-layer chromatography [silica gel, chloroform-methanol-water (65:25:4)]: Rf=0.32.

NMR (60 MHz, CDCl$_3$) δ: 0.94(9H), 1.28(32H), 1.45–1.78(8H), 3.02–4.05(12H), 3.38(9H), 4.21(2H), 4.98(1H).

IR(film)cm$^{-1}$: 2930, 2855, 1692, 1225, 1090, 1060.

EXAMPLE 41

2-(N,N-Dibutylcarbamoyloxy)-3-octadecyloxypropyl 2-dimethylaminoethyl phosphate

The bromide compound synthesized in the same manner as Examples 4 and 13 from 850 mg of the alcohol compound obtained in Example 39, 618 mg of 2-bromoethyl phosphorodichloridate, 202 mg of pyridine and 7 ml of benzene, was dissolved in 15 ml of 20% dimethylamine-in-toluene. The solution was allowed to stand at room temperature for 24 hours and then treated in the same manner as Examples 5 and 14 to give 133 mg (12.0%) of the above-identified compound as a colorless solid.

Thin-layer chromatography [silica gel, chloroform-methanol-water (65:25:4)]: Rf=0.56.

NMR (60 MHz, CDCl$_3$) δ: 0.91(9H), 1.25(32H), 1.42–1.82(8H), 2.88(6H), 3.01–4.49(15H), 5.02(1H).

IR(film)cm$^{-1}$: 2940, 2855, 1690, 2222, 1160, 1085.

EXAMPLE 42

3-Octadecyl-2-morpholinocarbonyl-1-tritylglycerol

3-Octadecyl-1-tritylglycerol (2.93 g) and 0.8 g of pyridine were dissolved in 10 ml of dichloromethane, and, under ice-cooling and stirring, 0.78 g of phenyl chlorocarbonate was added dropwise. The mixture was stirred under ice-cooling for 30 minutes and at room temperature for an hour, followed by addition of 20 ml of dichloromethane and water. The organic layer was separated, washed with aqueous sodium hydrogen carbonate and water, and dried. The solvent was then distilled off and 5 ml of morpholine was added to the residue. The mixture was allowed to stand at room temperature overnight and the morpholine was distilled off. The residue was recrystallized from n-hexane to give 2.7 g of the above-identified compound melting at 78°–79° C.

IR(Nujol)cm$^{-1}$: 1701, 1243.

NMR (60 MHz, CDCl$_3$) δ: 0.90(3H), 1.24(32H), 3.2–3.95(14H), 5.11(1H, m), 7.1–7.6(15H).

EXAMPLE 43

3-Octadecyl-2-morpholinocarbonylglycerol

The glycerol compound (2.7 g) obtained in Example 42 was dissolved in 30 ml of 80% acetic acid, and the solution was heated at 100° C. for an hour. The solvent was then distilled off and the residue was purified by silica gel column chromatography to give 1.3 g of the above-identified compound melting at 48°–49° C.

IR(Nujol)cm$^{-1}$: 3360, 1679, 1104.

NMR (60 MHz, CDCl$_3$) δ: 0.88(3H), 1.3(32H), 3.3–3.95(14H), 4.90(1H, m).

EXAMPLE 44

3-Octadecyloxy-2-morpholinocarbonyloxypropyl 2-bromoethyl phosphate

The glycerol compound (1.3 g) obtained in Example 43 and 0.82 g of 2-bromoethyl phosphorodichloridate were dissolved in 15 ml of benzene and, under ice-cooling and stirring, 0.272 g of pyridine was added dropwise. The mixture was stirred under ice-cooling for 10 minutes and at room temperature for an hour. The solvent was then distilled off and 30 ml of water was added to the residue. The mixture was refluxed for an hour and, after cooling, it was extracted with ether to give the desired bromide compound.

This product was divided into 1:1:2 portions which were reacted with trimethylamine, pyridine and thiazole in Examples 45, 46 and 47, respectively.

EXAMPLE 45

3-Octadecyloxy-2-morpholinocarbonyloxypropyl 2-trimethylammonioethyl phosphate

The bromide compound obtained in Example 44 was dissolved in 5 ml of trimethylamine-in-toluene and the solution was allowed to stand at room temperature for 3 days. The solvent was then distilled off and 500 mg of silver carbonate and 15 ml of methanol were added to the residue. The mixture was refluxed and the insoluble material was filtered off. The solvent was distilled off and the residue was purified by silica gel column chromatography to give 255 mg of the above-captioned compound.

IR(KBr)cm$^{-1}$: 3380, 2910, 2845, 1680, 1250, 1055.

NMR (60 MHz, CDCl₃) δ: 0.90(3H), 1.25(32H), 3.36(9H, s). 3.1–4.6(18H), 5.03(1H, m).

EXAMPLE 46

3-Octadecyloxy-2-morpholinocarbonyloxypropyl 2-pyridinioethyl phosphate

The bromide compound obtained in Example 44 was treated in the same manner as Examples 8, 15 and 32 to give the above-identified compound.

IR(film)cm$^{-1}$: 3350, 2910, 2840, 1690, 1250, 1072.

NMR (60 MHz, CDCl₃) δ: 0.88(3H), 1.24(32H), 3.2–4.7(16H), 4.98(3H), 7.9–8.7(3H), 9.2(1H).

EXAMPLE 47

3-Octadecyloxy-2-morpholinocarbonyloxypropyl 2-thiazolio ethyl phosphate

The bromide compound obtained in Example 44 was dissolved in 1 ml of thiazole. The solution was heated at 60° C. for 3 days and then treated in the same manner as Examples 21 and 33 to give the above-identified compound.

IR(film)cm$^{-1}$: 3370, 2910, 2845, 1692, 1250, 1070.

NMR (60 MHz, CDCl₃) δ: 0.90(3H), 1.26(32H), 3.2–4.7(16H), 4.96(3H), 8.26(1H), 8.56(1H), 10.62(1H).

EXAMPLE 48

2-(N,N-Dimethylcarbamoyloxy)-3-octadecyloxypropyl 2-dimethylaminoethyl phosphate The bromide compound (1.3 g) obtained in Example 18 was dissolved in 15 ml of 20% dimethylamine-in-toluene and the mixture was allowed to stand at room temperature overnight. After concentration, the residue was purified by silica gel column chromatography using methanol as the eluent to give 0.7 g of above-identified compound as colorless powder.

Thin-layer chromatography [silica gel, chloroform-methanol-water (65:25:4)]: Rf=0.4, single spot.

IR(KBr)cm$^{-1}$: 3400, 2910, 2850, 1700, 1472, 1200, 1090, 1065.

NMR (60 MHz, CDCl₃) δ: 0.88(3H), 1.26(32H), 2.76(6H,s), 2.88(6H, s), 3.0–4.4(10H), 4.92(1H, m).

EXPERIMENT

Hypotensive effect in spontaneously hypertensive rats

Experimental Method and Results

Male spontaneously hypertensive rats aged 11 weeks and with a blood pressure of about 200 mmHg were used in groups of 3 individuals. The control blood pressure of each rat was measured (by plethysmography) before the administration of each test compound and the test compound in the form of a 10 ml/kg aqueous solution was then orally administered at the dose level of 1 to 10 mg/kg.

At 1, 3 and 5 hours after administration, the blood pressure was similarly measured and the antihypertensive effect was evaluated based on the change in blood pressure from the pre-treatment control level. The results are shown in Table 1.

TABLE 1

| Compound (I) (Example No.) | Dosage mg/kg | Blood pressure before administration | Antihypertensive effect (fall in blood pressure), mmHg | | | |
|---|---|---|---|---|---|---|
| | | | After 1 hr. | After 3 hrs. | After 5 hrs. | After 24 hrs. |
| 19 | 1 | 233 ± 1 | −36 ± 2** | −65 ± 5** | −65 ± 3** | −57 ± 2** |
| 20 | 1 | 219 ± 4 | −28 ± 8 | −39 ± 13 | −40 ± 8* | |
| 21 | 1 | 219 ± 6 | −40 ± 5* | −59 ± 6* | −66 ± 3** | −34 ± 4* |
| 25 | 1 | 220 ± 6 | −23 ± 14 | −33 ± 3** | −39 ± 7* | |
| 14 | 10 | 179 ± 4 | −11 ± 2* | −11 ± 2* | −23 ± 4* | −25 ± 2** |

Students t-test (paired),
*P<0.05,
**P<0.01

Preparation Example

1. Tablets

| Composition: | |
|---|---|
| (1) 2-(N,N—Dimethylcarbamoyloxy)-3-octadecyloxypropyl 2-trimethylammonioethyl phosphate | 10 g |
| (2) Lactose | 85 g |
| (3) Corn starch | 20 g |
| (4) Hydroxypropyl-cellulose | 4 g |
| (5) Magnesium stearate | 1 g |
| 1000 Tablets | 120 g |

Preparation:

A mixture of ingredients (1), (2) and (3) is wetted with a 10% aqueous solution of the ingredient (4), passed through a 1.5 mm screen, and the granules are dried in vacuo at 40° C. The dry granules were further passed through the screen, mixed with the ingredient (5), and tableted to give 1000 tablets each measuring 7 mm in diameter and containing 10 mg of the ingredient (1).

2. Sugar-coated tablets

The above prepared tablets are coated with a coating composition comprising sucrose, talc and pulverized gum arabic. The coated tablets are polished with beeswax. Weight, per tablet, of the sugar-coated tablets: 250 mg. P 3. Capsules

| Composition: | |
|---|---|
| (1) 2-(N,N—Dimethylcarbamoyloxy)-3-octadecyloxypropyl 2-trimethylammonioethyl phosphate | 25 g |
| (2) Corn starch | 95 g |
| (3) Talc | 10 g |
| 1000 Capsules | 130 g |

Preparation:

All the above ingredients are blended and filled into 1000 gelatin capsules to give capsules each containing 25 mg of the ingredient (1).

4. Injections

In 1.0 l of distilled water is dissolved 5 g of 2-(N,N-dimethylcarbamoyloxy)-3-octadecyloxypropyl 2-trimethylammonioethyl phosphate, and after passage through a bacterial filter, the solution is distributed in 1 ml portions into 1000 vials. The solution in the vials are freeze-dried and the vials are sealed.

On the other hand, 2 l of a solution of 100 g of xylitol or mannitol in distilled water for injection is distributed in 2 ml portions into injection ampules which are then sealed to provide 1000 ampules.

In use, one vial equivalent of the former powder is dissolved in the xylitol (or mannitol) solution for injection.

What is claimed is:

1. A method of treatment of hypertension in a mammal, which comprises administering to said mammal an effective antihypertensive amount of a compound of the formula

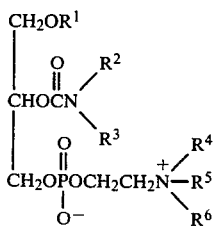

wherein $R^1$ is alkyl or alkylcarbamoyl containing 10 to 30 carbon atoms, $R^2$ and $R^3$ are independently hydrogen or $C_{1-6}$ alkyl or wherein $NR^2R^3$ are piperidino, morpholino, thiomorpholino, 1-piperazinyl, 1-pyrrolidinyl, 1-azetidinyl or 1-azilidinyl and

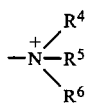

is a pyridinio, oxazolio, thiazolio, pyridazinio, quinolinio, isoquinolinio, N-methylmorpholinio, morpholinio, N-methylpiperazinio or piperazinio group, each of said groups being unsubstituted or substituted by one $C_{1-4}$ alkyl, hydroxy, hydroxyethyl, aminoethyl, amino, imino, carbamoyl or ureido group, or a pharmaceutically acceptable salt thereof.

2. A method for treatment for hypertension in a mammal, which comprises administering to said mammal an effective antihypertensive amount of a compound of the formula

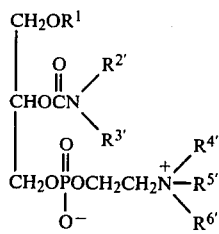

wherein $R^1$ is alkyl or alkylcarbamoyl containing 10 to 30 carbon atoms, $R^{2'}$ and $R^{3'}$ are $C_{1-6}$ alkyl or wherein $NR^{2'}R^{3'}$ are piperidino, morpholino, thiomorpholino, 1-piperazinyl, 1-pyrrolidinyl, 1-azetidinyl or 1-azilidinyl and $R^{4'}$, $R^{5'}$ and $R^{6'}$ are independently hydrogen or $C_{1-6}$ alkyl, or a pharmaceutically acceptable salt thereof.

3. A method according to claims 1 or 2, wherein $R^1$ is alkyl or alkylcarbamoyl containing 12 to 20 carbon atoms.

4. A method according to claims 1 or 2, wherein $R^1$ is n-octadecyl or n-octadecylcarbamoyl.

5. A method according to claim 1 or 2, wherein $R^1$ n-octadecyl.

6. A method according to claim 1 or 2, wherein $NR^2R^3$ or $NR^{2'}R^{3'}$ are thiomorpholino or 1-piperazinyl.

7. A method according to claim 1 or 2, wherein $NR^2R^3$ or $NR^{2'}R^{3'}$ are piperidino or morpholino.

8. A method according to claim 1 or 2, wherein $R^2$ and $R^3$ or $R^{2'}$ and $R^{3'}$ are methyl.

9. A method according to claim 8 wherein $R^4$, $R^5$ and $R^6$, together with the adjacent nitrogen atom, form a pyridino, oxazolio, thiazolio, pyridazinio, N-methylmorpholinio, morpholinio, N-methylpiperazinio or piperazinio group, each of said groups being unsubstituted or substituted by one $C_{1-4}$ alkyl, hydroxy, hydroxyethyl, aminoethyl, amino, imino, carbamoyl or ureido group.

10. A method according to claim 9 wherein $R^4$, $R^5$, and $R^6$, together with the adjacent nitrogen atom, form pyridinio, thiazolio or morpholino.

11. A method according to claim 2 wherein at least two of $R^4$, $R^5$ and $R^6$ are $C_{1-6}$ alkyl.

12. A method according to claim 2 wherein $R^{5'}$ and $R^{6'}$ are methyl.

13. A method of claim 1 wherein the compound is 2-(N-methylcarbamoyloxy)-3-octadecyloxypropyl 2-thiazolioethyl phosphate.

14. A method of claim 1 wherein the compound is 2-(N,N-dimethylcarbamoyloxy)-3-octadecyloxypropyl 2-pyridinioethyl phosphate.

15. A method of claim 1 wherein the compound is 2-(N,N-dimethylcarbamoyloxy)-3-octadecyloxypropyl 2-thiazolioethyl phosphate.

16. A method of claim 2 wherein the compound is 2-(N,N-dimethylcarbamoyloxy)-3-octadecyloxypropyl 2-trimethylammonioethyl phosphate.

17. A method of claim 2 wherein the compound is 2-(N,N-dimethylcarbamoyloxy)-3-(N-octadecylcarbamoyloxy)propyl 2-trimethylammonioethyl phosphate.

* * * * *